(12) United States Patent
Stalker et al.

(10) Patent No.: US 7,632,303 B1
(45) Date of Patent: *Dec. 15, 2009

(54) VARIABLE STIFFNESS MEDICAL DEVICES

(75) Inventors: Kent C. B. Stalker, San Marcos, CA (US); Masoud Molaei, Fremont, CA (US); John F. Boylan, Murrieta, CA (US); Matthew J. Gillick, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1391 days.

This patent is subject to a terminal disclaimer.

(21) Appl. No.: 10/152,150

(22) Filed: May 21, 2002

Related U.S. Application Data (63) Continuation-in-part of application No. 09/590,307, filed on Jun. 7, 2000, now Pat. No. 6,652,576.

(51) Int. Cl.
  *A61F 2/06* (2006.01)
(52) U.S. Cl. .................... 623/1.19; 623/1.15; 623/1.18; 623/1.2
(58) Field of Classification Search ....... 623/1.15–1.18, 623/1.19, 1.2, 1.22
See application file for complete search history.

(56) References Cited

U.S. PATENT DOCUMENTS

| | | | |
|---|---|---|---|
| 4,484,955 A | 11/1984 | Hochstein | |
| 4,665,906 A | 5/1987 | Jervis | |
| 4,881,981 A | 11/1989 | Thoma et al. | |
| 4,922,718 A | 5/1990 | Hochstein | |
| 4,969,890 A | 11/1990 | Sugita et al. | |
| 5,017,133 A | 5/1991 | Miura | |
| 5,025,799 A | 6/1991 | Wilson | |
| 5,067,957 A | 11/1991 | Jervis | |
| 5,190,546 A | 3/1993 | Jervis | |
| 5,366,504 A | 11/1994 | Andersen et al. | |

(Continued)

FOREIGN PATENT DOCUMENTS

DE    195 37 872 A 1    4/1997

(Continued)

OTHER PUBLICATIONS

Gupta, Subash, et al., Effect of Cold Work on Mechanical Properties and on TTR's of a Nickel Titanium Shape Memory Alloy, Proceedings of the Second International Conference on Shape Memory and Superelastic Technologies, Asilomar Conference Center, Pacific Grove, California pp. 41-46, 1997.

(Continued)

*Primary Examiner*—(Jackie) Tan-Uyen T. Ho
*Assistant Examiner*—Melanie Tyson
(74) *Attorney, Agent, or Firm*—Fulwider Patton LLP (57) ABSTRACT

A medical device has a structure differentiated in terms of its stiffness or elasticity. Such stiffness differentiation is achieved through the use of superelastic or shape-memory materials which transition between a relatively malleable phase to a stiffer phase at a transition temperature which is adjustable by heat treatment. A differentiation of the stiffness of the structure forming the medical device is achieved by differentially adjusting the transition temperature of select portions of the medical device before the medical device is placed in its operational mode, usually implanted in a body at body temperature.

15 Claims, 3 Drawing Sheets

U.S. PATENT DOCUMENTS

| | | |
|---|---|---|
| 5,383,892 A | 1/1995 | Cardon et al. |
| 5,395,390 A | 3/1995 | Simon et al. |
| 5,413,597 A | 5/1995 | Krajicek |
| 5,421,955 A | 6/1995 | Lau et al. |
| 5,449,373 A | 9/1995 | Pinchasik et al. |
| 5,476,506 A | 12/1995 | Lunn |
| 5,486,183 A | 1/1996 | Middleman et al. |
| 5,509,923 A | 4/1996 | Middleman et al. |
| 5,514,115 A | 5/1996 | Frantzen et al. |
| 5,514,154 A | 5/1996 | Lau et al. |
| 5,569,295 A | 10/1996 | Lam |
| 5,597,378 A | 1/1997 | Jervis |
| 5,601,593 A | 2/1997 | Freitag |
| 5,632,746 A | 5/1997 | Middleman et al. |
| 5,674,276 A | 10/1997 | Andersen et al. |
| 5,716,393 A | 2/1998 | Lindenberg et al. |
| 5,720,754 A | 2/1998 | Middleman et al. |
| 5,749,879 A | 5/1998 | Middleman et al. |
| 5,820,628 A | 10/1998 | Middleman et al. |
| 5,836,966 A | 11/1998 | St. Germain |
| 5,855,600 A | 1/1999 | Alt |
| 5,861,027 A | 1/1999 | Trapp |
| 5,868,780 A | 2/1999 | Lashinski et al. |
| 5,876,434 A | 3/1999 | Flomenblit et al. |
| 5,904,657 A | 5/1999 | Unsworth et al. |
| 5,904,690 A | 5/1999 | Middleman et al. |
| 5,911,754 A | 6/1999 | Kanesaka et al. |
| 5,922,021 A | 7/1999 | Jang |
| 5,938,697 A | 8/1999 | Killion et al. |
| 5,954,743 A | 9/1999 | Jang |
| 5,964,744 A | 10/1999 | Balbierz et al. |
| 6,004,330 A | 12/1999 | Middleman et al. |
| 6,010,530 A | 1/2000 | Goicoechea |
| 6,027,526 A | 2/2000 | Limon et al. |
| 6,053,943 A | 4/2000 | Edwin et al. |
| 6,066,168 A | 5/2000 | Lau et al. |
| 6,071,298 A | 6/2000 | Lashinski et al. |
| 6,106,548 A | 8/2000 | Roubin et al. |
| 6,106,642 A | 8/2000 | DiCarlo et al. |
| 6,146,403 A | 11/2000 | St. Germain |
| 6,254,550 B1 | 7/2001 | McNamara et al. |
| 6,485,507 B1 | 11/2002 | Walak et al. |
| 6,652,576 B1 | 11/2003 | Stalker |

FOREIGN PATENT DOCUMENTS

| | | |
|---|---|---|
| EP | 0 800 801 A 1 | 10/1997 |
| EP | 0 830 853 A 1 | 3/1998 |
| WO | WO 98/22159 | 5/1998 |
| WO | WO 98/48734 | 11/1998 |
| WO | WO 01/93783 A2 | 12/2001 |

OTHER PUBLICATIONS

Duerig, T.W., et al., An Engineer's Perspective of Pseudoelasticity, Source Unknown, pp. 369-393, Undated.

Zadno, G.R., et al., Linear Superelasticity in Cold-Worked Ni-Ti, Source Unknown, pp. 414-419, Undated.

Schetsy, L. McDonald, "Shape Memory Alloys," Scientific American, vol. 281, pp. 74-82 (Nov. 1979).

VARIABLE STIFFNESS MEDICAL DEVICES

CROSS REFERENCE TO RELATED APPLICATION

This application is a continuation-in-part application of application having U.S. Ser. No. 09/590,307, filed Jun. 7, 2000 now U.S. Pat. No. 6,652,576, entitled VARIABLE STIFFNESS STENT, the entire contents of which are hereby incorporated by reference.

BACKGROUND OF THE INVENTION

This invention relates generally to the application of nickel-titanium alloys to medical devices and, more particularly, to medical devices made from superelastic materials, such as nickel-titanium alloy, which exhibit a differentiated degree of stiffness throughout selected portions of the structural device. Medical devices made in accordance with the present invention can be designed to be implanted either permanently or for a specific duration in a patient's body for medical treatment or can be used in the performance of a medical procedure.

Nickel-titanium alloy is a well known metal alloy possessing both shape memory and superelastic characteristics and has been used in medical device applications since this material possesses unique properties under certain conditions. Nickel-titanium alloy possesses both high elasticity and useful shape memory characteristics and is highly biocompatible, kink resistant, fatigue resistant, and has other beneficial engineering attributes which make the material particularly useful in medical applications.

The shape memory effect characteristic of nickel-titanium alloy is a result of metallurgical phase transformations. Depending on its temperature, the structural properties of nickel-titanium alloy enable it to function in two different states or phases. At the lower temperature range, below a specified transition temperature, nickel-titanium alloy loses rigidity and becomes soft and malleable and is said to be in a martensitic state or phase. However, when heated above the specified transition temperature, the nickel-titanium alloy transforms into its predetermined heat set shape and has relatively high tensile strength. In this physical state, nickel-titanium alloy is said to be in an austenitic state or phase. The shape memory properties of nickel-titanium alloy enable it to "remember" a particular shape instilled during a previous heat-set operation and to transform back to that shape when desired. Nickel-titanium alloy also can be permanently shaped by annealing with extreme heat, or by coldworking which involves plastically deforming the material.

In terms of its elasticity, nickel-titanium alloy can become highly elastic under certain conditions and is able to experience extensive deformation, yet is capable of transforming back to its original shape. Nickel-titanium alloys are known to exhibit "pseudoelastic" or "superelastic" behavior when subjected to certain cold working processes or cold working and heat treatment processes following hot working. This beneficial attribute of nickel-titanium alloy refers to the ability of the material to undergo extremely large elastic deformation, in the order of 8% or more when stressed, and to substantially fully recover all strain upon removal of the stress without adversely affecting its memory properties. Full recovery is typically understood to be less than 0.5 percent unrecovered strain, also known as permanent set or amnesia.

These characteristics allow a medical device made from nickel-titanium alloy to be deformed and restrained in a deformed condition, enabling the device to be delivered in a compressed condition into the patient's body. The deformation of the material usually causes a phase transformation to occur, e.g., austenite to martensite. Once the medical device is placed in the target area of the body, the restraint can be removed to reduce the stress on the device and allow it to return to its original pre-deformed shape within the body. This results in the material transforming back to its original austenite phase from the martinsitic phase. This phenomenon of reversible phase transformation from austenite to martensite is more precisely called "stress-induced martensite" (SIM).

Because of the useful nature of the nickel-titanium alloy, some have attempted to change its properties to solve different design needs. For example, U.S. Pat. No. 6,106,642 to DiCarlo et al. discloses annealing nickel-titanium alloy to achieve improved ductility and other mechanical properties. U.S. Pat. No. 5,876,434 to Flomenblit et al. teaches annealing and deforming nickel titanium alloy to obtain different stress-strain relationships. Some medical device related applications exploit the non-linear pseudoelastic capabilities of nickel titanium. Examples include: U.S. Pat. Nos. 4,665,906; 5,067,957; 5,190,546; and 5,597,378 to Jervis; and U.S. Pat. Nos. 5,509,923; 5,486,183; 5,632,746; 5,720,754; and 6,004,629 to Middleman, et al.

As briefly described above, superelasticity or pseudoelasticity refers to the highly exaggerated elasticity or spring-back observed in many nickel-titanium alloys deformed above their austenite finish temperature ($A_f$) and below the martensite deformation temperature ($M_d$). Hence, nickel-titanium alloys can deliver over fifteen times the elasticity of spring steel. The martensite deformation temperature ($M_d$) is defined as the temperature above which martensite cannot be stress-induced. Consequently, nickel-titanium alloy remains in its austenitic phase throughout an entire deformation above $M_d$.

In one particular medical application, nickel-titanium alloy has found use in self-expanding stents. Historically, stents were not self-expanding but rather were expanded and deployed by a balloon catheter. Balloon expanded stents are used in conjunction with balloon angioplasty procedures with the intent to reduce the likelihood of restenosis of a diseased vessel. Stents are also used to support a body lumen, tack-up a flap or dissection in a vessel, or in general where the lumen is weak to add support.

For balloon expandable stents, the stent is positioned over the balloon portion of a catheter and is expanded from a reduced delivery diameter to an enlarged deployment diameter greater than or equal to the inner diameter of the arterial wall by inflating the balloon. Stents of this type are expanded to an enlarged diameter through deformation of the stent, which then engages the vessel wall. Eventual endothelial growth of the vessel wall covers the stent.

Nickel-titanium alloy found use in self-expanding stents, where deployment was a result of either shape-memory effect or superelasticity in the material rather than by use of a dilatation balloon. The stent once released from its delivery system assumed a pre-set shape in the particular body lumen. Such self-expanding stents can be used to scaffold a number of body vessels, including the inside circumference of a tubular passage such as an esophagus, bile duct, or blood vessel.

The benefits of using a superelastic nickel-titanium material for self-expanding stents are primarily related to its large recoverable strain. The biocompatibility of nickel-titanium alloy is also an attractive benefit for use of this material in stenting applications, because the stent remains in the patient as part of the treatment.

The use of nickel-titanium alloy to form a balloon-expandable stent has been less common. The balloon-expandable and scaffolding capabilities of such stents are accomplished by setting the austenite finish temperature ($A_f$) at about 55° C. or well above body temperature. The entire stent is therefore completely martensitic before, during, and after balloon deployment. This may be perceived as a disadvantage since the balloon-expandable nickel-titanium alloy stent remains in its martensitic phase and is somewhat soft. The scaffolding function and hoop strength of such a stent can be somewhat diminished.

This is not to say that a select portion of a stent, or other medical device, which remains in a martensitic state at body temperature is a disadvantage. Rather, certain benefits can be achieved from a stent, or other medical device, having a portion of the device remaining in a martensitic state while the remainder of the device assumes an austenitic state. For example, stents have a tendency to restenose more at their ends. This phenomenon may be prevented by making the ends of the stent, either at one end or both ends, less stiff by design or processing. In this regard, it may be beneficial if the ends of the stent are maintained in the softer martensitic state while the remainder of the stent assumes an austenitic state. Additionally, a stent or graft which is to be implanted in a body vessel having different inner diameters can be problematic to the engineer. One such example occurs when a stent is to be implanted at a bifurcated vessel in which the primary vessel has larger diameter than an adjacent side branch vessel. If the self-expanding stent exerts a uniform radial force when deployed, it is possible for the portion of the stent implanted in the smaller diameter vessel to deploy a greater outward radial force on the vessel wall than the portion of the stent implanted in the larger diameter vessel. In some instances, a larger than needed radial force on the wall of a body vessel could possibly cause unnecessary trauma to the vessel.

What has been needed in medical engineering is a medical device incorporating select portions of nickel-titanium alloy maintained in an austenitic phase with select portions maintained in a martensetic phase when the device assumes its operational state (usually implanted in the patient's body at body temperature). In this manner, such a medical device should develop variable stiffness depending on whether the portion of the device is maintained in a martensitic or austenitic phase. Once such medical device is placed in its operational state, the device should have selected portions or regions that remain stiffer than other portions or regions. Such a variable stiffness medical device would also be beneficial if it is available for medical applications including, but not limited to, stents, guide wires, guide catheters, embolic filtering devices and endovascular grafts. Moreover, it is most desirable to provide a manufacturing process by which the stiffness of various components of the medical device can be adjusted quickly and easily to suit the requirements of a particular type of application. The present invention satisfies these and other needs.

SUMMARY OF THE INVENTION

The present invention provides a medical device that exhibits a differentiated degree of stiffness or elasticity throughout selected portions of its structure. In accordance with the present invention, the stiffness of the medical device is readily differentiated throughout its structure when manufactured in any one of a number of configurations. The device's stiffness may thereby be reduced in those areas where, for example, less developed structural force is needed to reduce the possibility of traumatization of tissue that comes in contact with the medical device. Such stiffness differentiation is achieved with the differentiated heat treatment of selected portions or elements of the medical device after its fabrication. This provides a further advantage in that a single, unitary structure can be tailored to accommodate specific requirements of many different types of deployment sites and different physical applications within the patient's body. Such medical devices, when formed into a self-expanding stent, for example, overcome certain disadvantages associated with certain prior art stents by exerting less force on the vessel walls while still providing the necessary support needed at other locations along the stent to properly scaffold the body vessel.

The desired differentiation in the stiffness of a medical device made in accordance with the present invention is achieved by the use of a superelastic or shape memory material in its construction, such as nickel-titanium alloy, wherein such material undergoes a transition from a relatively soft and malleable phase to a relatively strong and stiff phase as the temperature of the material is raised through a transition temperature. Approaching the transition temperature from a lower temperature causes the material to become stronger and stiffer while approaching such temperature from a higher temperature causes the material to become softer and more malleable. Special localized heat treatment of the material serves to shift the transition temperature of select portions of the structure to a higher temperature. In this manner, localized heat treatment of select portions of the composite medical device serves to shift the transition temperature of only those portions to a higher temperature. By shifting the transition temperature of select portions of the medical device closer to body temperature, i.e., to nearer the temperature at which the medical device will be maintained upon deployment, such portions tend to be in a softer and more malleable state than those portions of the device wherein the transition temperature has not been shifted or has been shifted to a lesser degree.

The desired differentiation may be achieved either by subjecting only those portions of the medical device which are to be softer and more malleable to an elevated temperature or by subjecting the entire device to an elevated temperature while maintaining those portions which are to remain strong and stiff in contact with a heat sink. A number of different forms of heat sources could be used to supply the necessary heat energy in order to achieve a certain shift whereby the total heat energy that is supplied is a function of both temperature and total time of exposure to such temperature.

In one aspect of the invention, the structure forming the medical device can be a self-expanding stent which is heat treated such that the end portions of the stent are in a softer and more malleable state than its center portion once the stent is subjected to body temperature. The center portion of the stent is thereby able to provide the necessary support to the vessel wall while its ends are less likely to become excessively embedded in the vessel tissue. As a result, the risk of restenosis is reduced.

In an alternative embodiment, the stiffness of only one end of the stent is reduced in order to enable the stent to more uniformly support a tapered deployment site or a deployment site that extends across a bifurcation. The change in stiffness may be relatively abrupt or may be distributed over a significant portion of the stent. By positioning the more malleable end of the stent in the smaller region of the vessel, traumatization of the vessel tissue is less likely. The risk of restenosis is thereby correspondingly reduced.

In a further alternative embodiment, the longitudinal stiffness of the entire stent is reduced without a reduction in its radial stiffness. This enables the entire stent to more uniformly conform to the vessel walls of a non-linear deployment site without compromising the stent's ability to support the vessel walls. The stent ends are therefore less likely to become excessively embedded in the vessel tissue to thus reduce the risk of restenosis.

The superelastic or shape memory material used to form the present invention can be nickel-titanium alloy, commonly referred to as Nitinol, an acronym for Nickel-Titanium Naval Ordinance Laboratory, when it was initially developed. The temperature at which the transition from the relatively soft and malleable martensitic phase to the relatively strong and stiff austenitic phase is completed is commonly referred to as the A(f). A 10° C. to 30° C. shift in the A(f) in the specially treated Nitinol can yield a difference in stiffness of up to about 50%.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention is directed to a medical device, and the process for forming the same, which exhibits a differentiated degree of stiffness at selected locations of its structure. Stiffness is similar to elasticity in that the medical device can have higher degrees of elasticity at select portions of the device. In the case of a stent, such differentiation may be limited to the longitudinal stiffness versus the radial stiffness of the stent or may include both longitudinal as well as radial stiffness differentiation in certain areas of its structure. The invention allows a fabricated stent's stiffness characteristics to be tailored to more effectively accommodate specific types of deployment sites. For illustration purposes, the following exemplary embodiments are typically shown as vascular stents. However, it is recognized that the present invention is not limited to such applications and rather may be used in various other medical devices (e.g., guide wires, endovascular grafts, embolic filtering cages) where the same principles are applicable.

Figure 1:
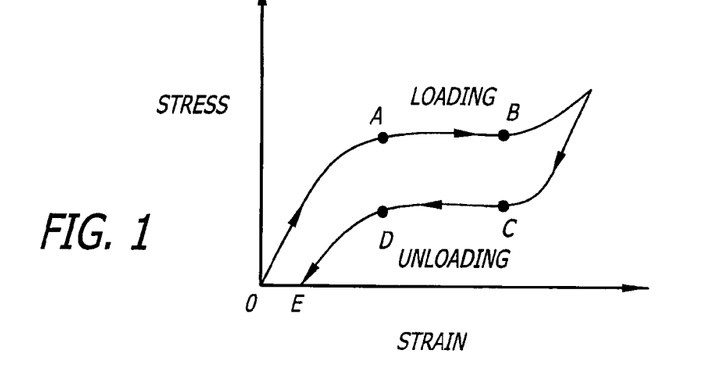
FIG. 1 is a standard stress-strain hysteresis curve for a nickel-titanium superelastic alloy.

Referring to FIG. 1, a stress-strain hysteresis curve for a binary nickel-titanium alloy demonstrating the loading and unloading of the metal alloy is shown. A more detailed discussion of nickel-titanium alloy behavior may be found in T. W. Duerig, A. R. Pelton, "Ti—Ni Shape Memory Alloys, Materials Properties Handbook Titanium Alloys," pp. 1035-1048, ASM International (1994), the contents of which are incorporated herein by reference. Additional industry literature by D. E. Hodgson, J. W. Brown, "Using Nitinol Alloys," pp. 1-38, Shape Memory Applications, Inc. (2000), provides an overview of the phenomenon of the shape memory effect exhibited by Nitinol, the contents of which are incorporated herein by reference. With regard to the use of Nitinol for medical device applications, particularly for guide-wire applications, the article by A. R. Pelton et al., "Optimisation of Processing and Properties of Medical Grade Nitinol Wire," pp. 107-118, Minimally Invasive Therapy & Allied Technologies (2000), provides an in-depth discussion in this area, the contents of which are incorporated herein by reference.

As illustrated in FIG. 1, the curve is also generally known as a superelastic curve which is characterized by areas of nearly constant stress during loading and unloading of the metal alloy. The line segment A-B, as depicted in FIG. 1, is the constant loading stress and is referred to as the loading plateau stress while the line segment C-D is the constant unloading stress and is referred to as the unloading plateau stress. The permanent set of the material in which strain is not recoverable is represented by the distance between point E and the origin O of FIG. 1.

The stress-strain hysteresis curve, as depicted in FIG. 1, is for a nickel-titanium alloy tested above its austenitic finish temperature ($A_f$) but below its martensite deformation temperature ($M_d$). The austenite finish temperature ($A_f$) is the temperature at which the nickel-titanium alloy completely converts to austenite. The onset of superelasticity occurs in the narrow temperature range just above $A_f$. The superelasticity performance of the nickel-titanium alloy steadily declines while approaching the martensite deformation temperature ($M_d$), at which point stress-induced martensite no longer appears and all superelasticity is hence eliminated.

The curve depicted in FIG. 1 represents the temperature range just above $A_f$ where superelasticity does occur. In such case, as the material is stressed, the curve is represented by sloped line O-A in which the material is completely austenitic. The transformation from austenite to stress-induced martensite (SIM) occurs at generally labeled point A indicated in FIG. 1. At a particular theoretical stress level, maintaining constant stress completely converts the austenite to stress-induced martensite in the nickel-titanium alloy, as represented by line segment A-B. Further application of stress beyond point B creates elastic deformation in the stress-induced martensite. A continuous application of stress leads to elastic deformation, represented by an upward slope, then plastic deformation, which is not shown in FIG. 1, in the stress-induced martensite.

The slope of the curve depicted in FIG. 1 reverses from beyond point B, dropping down to point C, as a result of the release of stress. Generally, at about point C, initial conversion of stress-induced martensite back to austenite occurs. At a certain stress level, as represented by line segment C-D, the material converts entirely from the stress-induced martensitic phase to the austenitic phase. Further release of the applied stress is represented by sloped line D-E which in turn represents the elastic deformation of the austenitic phase. As previously mentioned above, the permanent set of unrecoverable strain in the material is represented by strain E.

The aforementioned references to FIG. 1 serves to provide a brief overview of the unique mechanical properties of the alloy, nickel-titanium, which relates to the present invention.

Figures 2, 3:
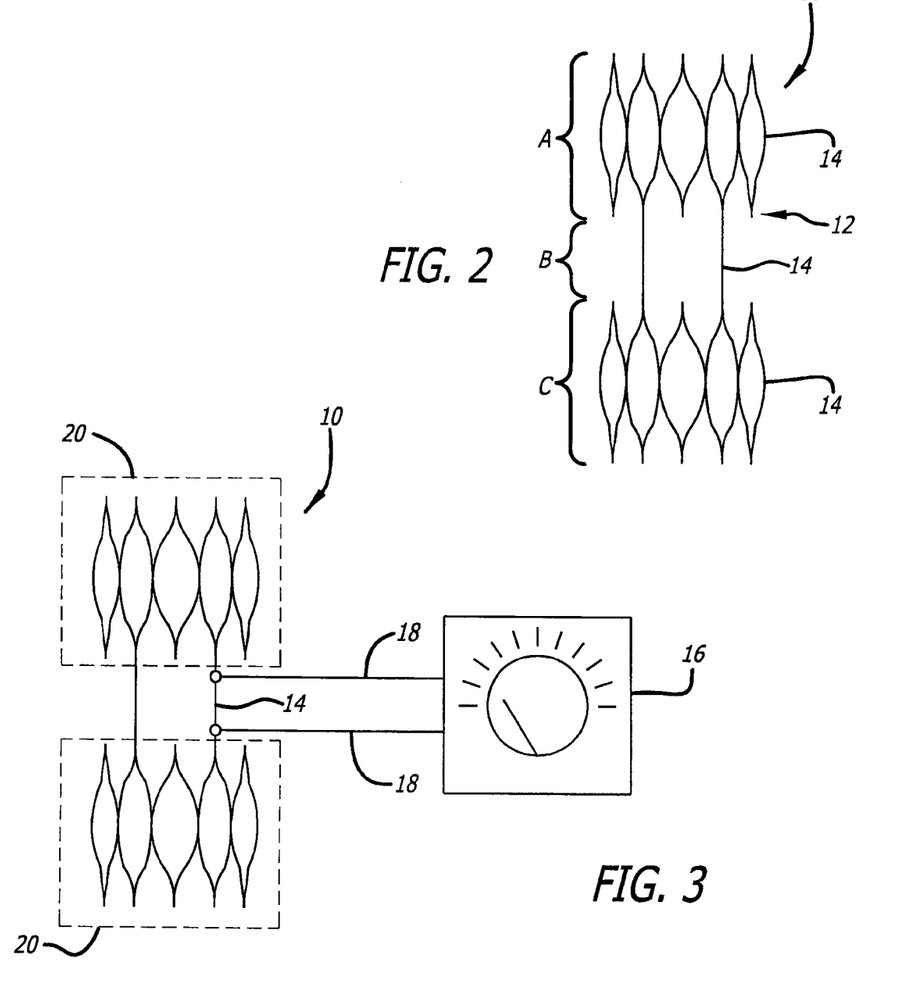
FIG. 2 is a schematic of a representative medical device embodying features of the present invention.
FIG. 3 is a schematic of one embodiment of an apparatus for selectively heating portions of a medical device to create a localized martensitic portion.

FIG. 2 is a general depiction of a medical device 10 in the form of a structural element 12 that includes struts 14 forming a portion A, portion B and portion C. The structural element 12 can be, for example, tubular in shape to form a stent or the underlying scaffolding for a vascular graft. The struts 14 in portions A and C can be self expanding and remain open during expansion of the medical device 10 to provide radial support to, for example, the wall of a body vessel. Portions A and C are representative of sections of the structural element which would remain somewhat stiff once deployed in the body. In this regard, Portions A and C are processed to remain in an austenitic phase once the device assumes its operational mode or state (usually implanted in the body at body temperature). Portion B, on the other hand, represents the softer and more malleable section of the structural element which remains in a martensitic phase when placed in its operational mode. The composite structural element thus has sections (Portions A and C) which remain stiffer than other sections (Portion B) of the structural element. It should be appreciated that the medical device can be formed in any number of shapes and configurations and can be used in numerous medical applications. While the medical device as formed is shown as a structural element including struts forming Section A, Section B, and Section C, it should be appreciated that the device can be made with simply only two portions, one of which is maintained in an austenitic phase during its operational mode while the other portion is maintained in a martensitic phase during use. Additionally, although the device is shown as a tubular shaped structural element, it could be a single elongated core of wire which could be utilized, for example, to create a portion of a guide wire or other medical device in which a single strand of wire or a plurality of wires form the structural element.

Preferably, the superelastic or shape memory material can be nickel-titanium alloy (Nitinol), however, other suitable alloys also are contemplated. The shape memory characteristics allow the devices to be deformed to facilitate their insertion into a body lumen or cavity and then to be heated within the body so that the device returns to its original shape.

Shape memory characteristics can be imparted to the alloy by heating the metal to a temperature above which the transformation from the martensitic phase to the austenitic phase is complete; i.e., a temperature above which the austenitic phase is stable. The shape of the metal during this heat treatment is the shape "remembered." The heat-treated metal is cooled to a temperature at which the martensitic phase is stable, causing the austenitic phase to transform to the martensitic phase. The metal in the martensitic phase is then plastically deformed, e.g., to facilitate the entry thereof into a patient's body. Subsequent heating of the deformed martensitic phase to a temperature above the martensite to austenite transformation temperature causes the deformed martensitic phase to transform to the austenitic phase. During this phase transformation the metal reverts back to its original shape.

The recovery or transition temperature may be altered by making minor variations in the composition of the metal and in processing the material. In developing the correct composition, biological temperature compatibility must be determined in order to select the correct transition temperature. In other words, when the medical device is heated, it must not be so hot that it is incompatible with the surrounding body tissue. Other shape memory materials may also be utilized, such as, but not limited to, irradiated memory polymers such as autocrosslinkable high density polyethylene (HDPEX).

Shape memory alloys undergo a transition between an austenitic state and a martinsitic state at certain temperatures. When they are deformed while in the martinsitic state they will retain this deformation as long as they are retained in this state, but will revert to their original configuration when they are heated to a transition temperature, at which time they transform to their austenitic state. The temperatures at which these transitions occur are affected by the nature of the alloy and the condition of the material. Nickel-titanium-based alloys, wherein the transition temperature is slightly lower than body temperature, are preferred for the present invention. It is desirable to have the transition temperature set at just below body temperature to insure a rapid transition from the martinsitic state to the austenitic state when the medical device is implanted in the body.

As is well known in the art, nickel-titanium alloy may undergo a transition from its martensitic phase to its austenitic phase under certain conditions including when its temperature is increased through a phase transition zone. The temperature at which the transition of martensite to austenite "starts" is referred to as the A(s) while the temperature at which its transformation to austenite is "finished" is commonly referred to as the A(f). While in its martensitic phase, the material is relatively in a soft and malleable state but upon heating becomes relatively stiffer and stronger as it approaches transition into its austenitic phase. The temperature range in which the transition occurs is affected by the heat energy that is absorbed during its heat treatment. A higher temperature and/or longer exposure to heat treatment will cause the A(f) to shift upwardly. A medical device having a nickel-titanium alloy structure with an A(f) that has been shifted nearer to body temperature will cause the device to be in a softer and more malleable state upon being deployed within the body than a device formed of a nickel-titanium alloy structure having an A(f) at a lower temperature. Similarly, a device having a nickel-titanium alloy structure with an A(f) that has been shifted beyond body temperature will cause the device to be in a softer and more malleable state upon being deployed within the body than a device having an A(f) that is closer to body temperature or below body temperature. The present invention provides for the selective adjustment of the A(f) in different areas or different individual elements of the same medical device after its fabrication. Upon deployment, those areas or elements of the medical device having a higher A(t) will be in a softer and more malleable state than areas or elements with a lower A(f). The reduced stiffness will cause the affected portion of the medical device to exert less force in an effort to attain its set shape.

A medical device made in accordance with the present invention also may be of the pseudoelastic variety (or other pseudoelastic alloys), which exhibits stress-induced martinsite properties. In such an embodiment, the medical device may undergo a transition from its austenitic phase to its martinsitic phase by the application of stress. When the stress is removed, the alloy will transform from the martinsitic phase to the austenitic phase without a change in temperature (isothermally). It should be appreciated that a medical device made with a pseudoelastic material is still processed in the same manner, namely, the particular shape of the structural element is first formed using techniques well known in the art, for example, chemical etching, or laser ablation. After the structural element is formed, select portions of the structural element can then be processed to change the transition temperature of that portion of the structural element in order to achieve the desired austenitic or martensitic phase once the medical device assumes its operational mode. In this manner, the medical device can still be transformed such that the portions of the structural element which assume the austenitic phase will undergo a transition to the martensitic phase once the appropriate stress is applied to the structural device. The portion of the structural element which is heat treated to remain in the martensitic phase during the operational mode will remain in its martensitic phase even upon further applications of stress, hence there will be no phase transformation upon applications of stress. Thereafter, once the stress is removed from the structural element, the portion or portions of the structural element which undergo phase transformation will now revert to the more rigid austenitic phase while those portions of the structural element which are adapted to remain in the martensitic phase still remain in the martensitic phase once the stress has been removed. Thus, the structural element will revert to its operational mode with a portion or portions remaining in an austenitic phase along with a portion or portions of the structural element being maintained in the martensitic phase.

Referring now to FIG. 3, a schematic representation of one apparatus which can be utilized to selectively heat process the medical device is shown. FIG. 3 shows a schematic representation of a power source 16 having a variable voltage source which can be attached to select portions of the structural element 12 to process the nickel-titanium alloy in order to change the thermal mechanical properties of the material. As is shown in FIG. 3, wires 18 are attached to the power source and are also attached to, for example, a strut 14 which forms a part of Portion B of the medical device 10. Electrical voltage can be applied to Portion B for a given time, until the desired properties of the nickel-titanium alloy are achieved. Depending upon the voltage and the time applied, Portion B can become a very soft martensitic material and will remain in its martensitic phase even the device assumes its operational mode. When processing the medical device 10, it is important that Portions A and C are not subjected to the heat treatment, since these particular sections of the medical device will be maintained at a different transformation temperature than the transformation temperature of Portion B. In this regard, Portions A and C of device 10 can be refrigerated (chilled) while Portion B is being heat treated. Dotted lines 20 surrounding Portions A and B in FIG. 3 depict a representative refrigeration source which can be placed around these particular portions of the device during processing. As a result, Portions A and C will maintain the original transformation temperature of the nickel-titanium alloy. The transformation temperature of Portion B, after heat treatment, will be different from Portions A and C. The resulting structural element will now have variable stiffness at select portions of the structural element. This is just one example of how the medical device can be processed. It should be appreciated that other variations from this example can be employed without departing from the scope of the present invention. Again, depending upon the temperature at which the medical device will be used during its operational state, the transition temperatures of the particular portions forming the structural element can be varied as desired in order to create the desired differential stiffness along the structural element. In this manner, a multiphase medical device can be manufactured.

Figure 4:
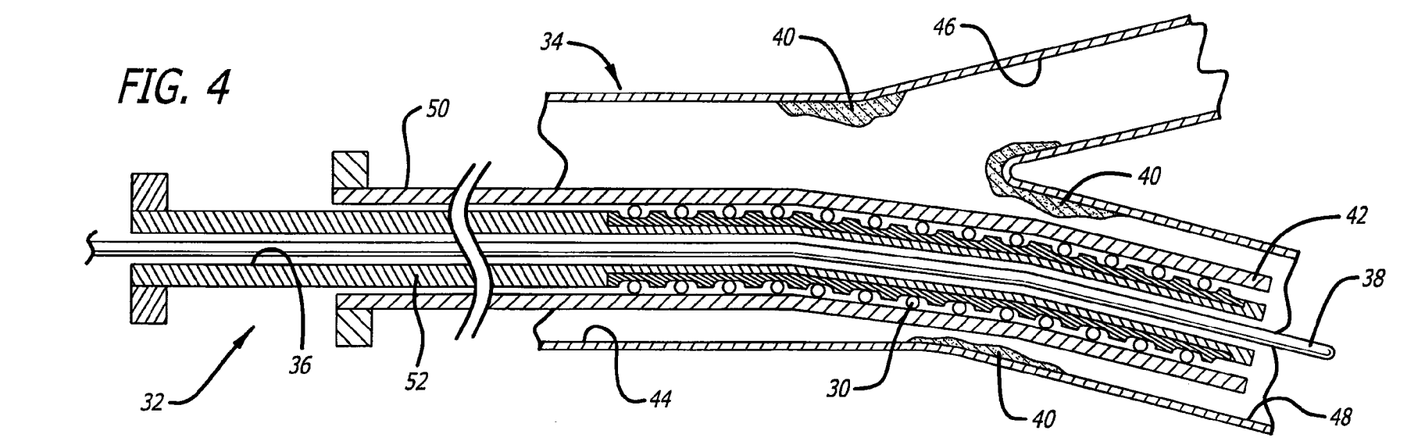
FIG. 4 is an elevational view, partially in cross section, of an over-the-wire catheter-delivery system with a self-expanding stent embodying features of the present invention as it is being positioned within a bifurcated body vessel.
Figure 5:
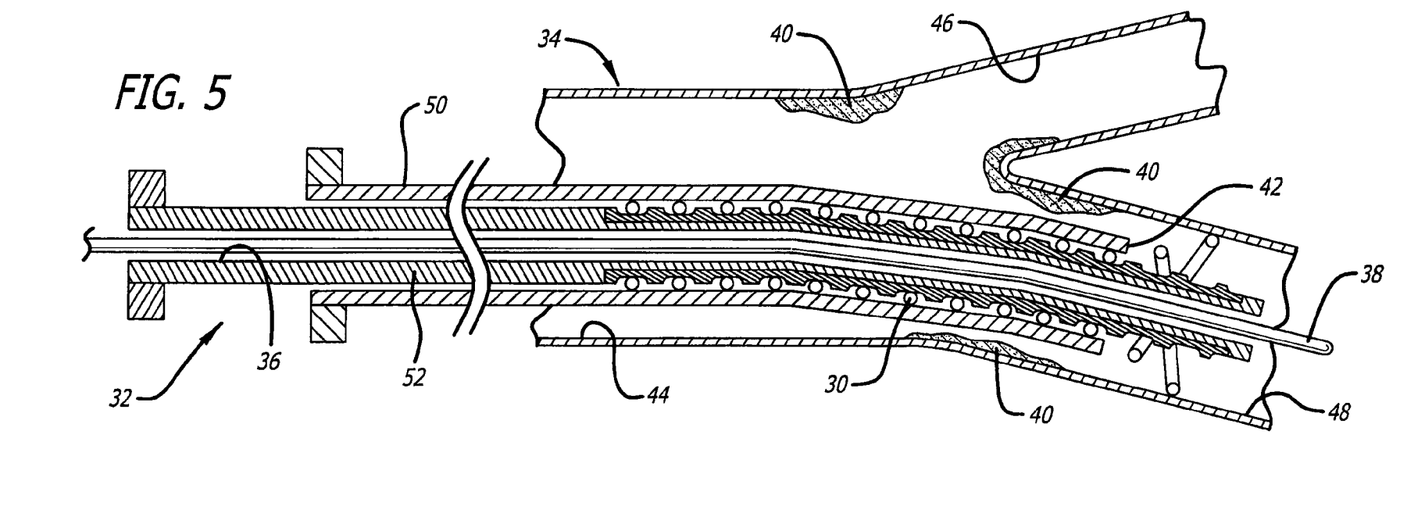
FIG. 5 is an elevational view, partially in cross section, depicting the over-the-wire catheter-delivery system of FIG. 4 in which the outer restraint is being retracted proximally to allow a portion of the self-expanding stent to expand radially outwardly to contact the wall of the side branch vessel.
Figures 6, 7, 8:
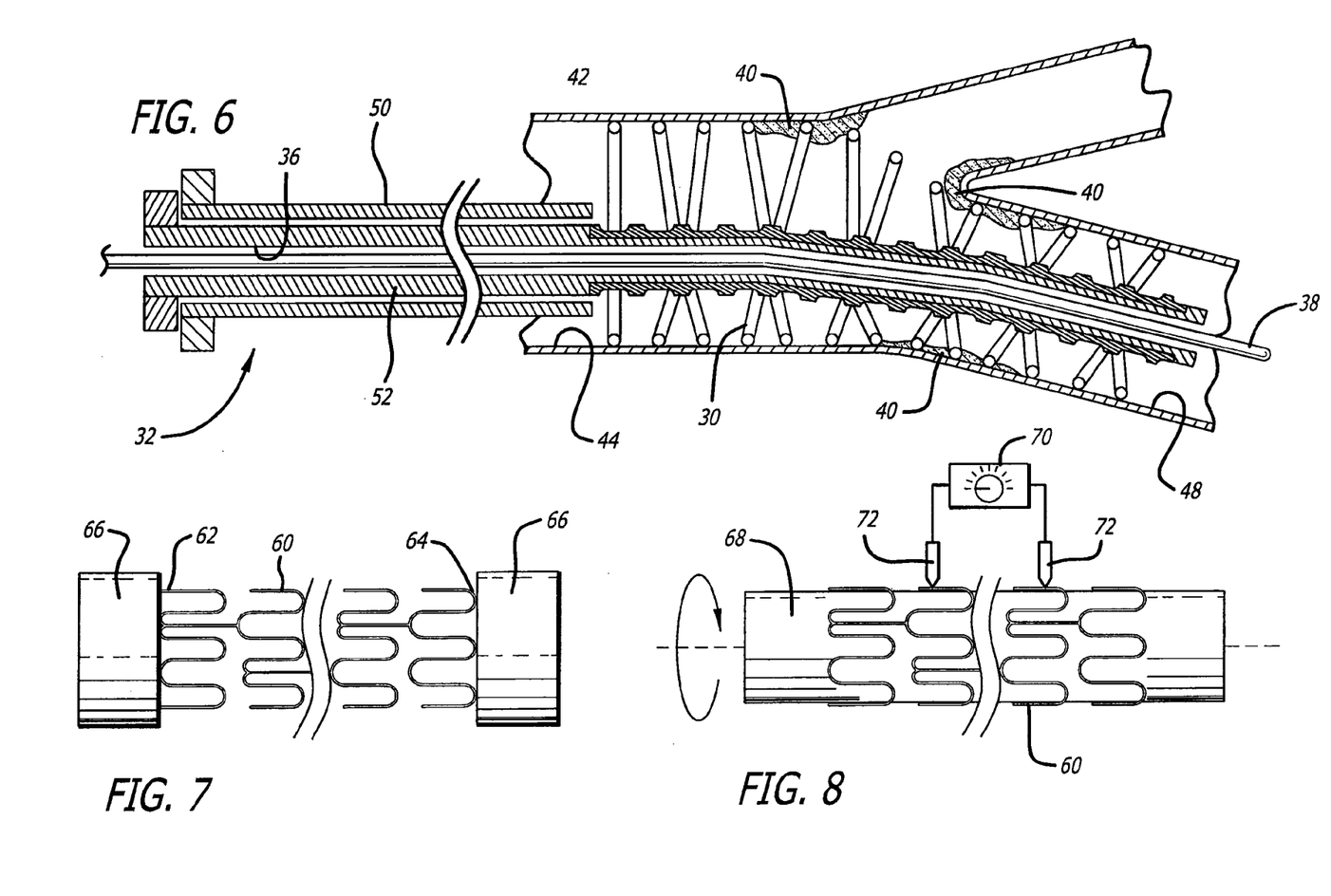
FIG. 6 is an elevational view, partially in cross section, depicting the stent of FIGS. 4 and 5 being implanted and contacting the wall of the main vessel and the wall of the side branch vessel.
FIG. 7 is a schematic view of one embodiment of an apparatus for selectively heating sections of a medical device to create a localized martensitic portion.
FIG. 8 is a schematic view of another embodiment of an apparatus for selectively heating sections of a medical device to create a localized martensitic portion.

In one exemplary application, nickel-titanium alloy is used to fabricate a stent 30. FIG. 4 is a schematic view of an over-the-wire catheter-delivery system 32 in which the stent 30 is being positioned at a bifurcated body vessel 34. Other delivery systems, such as the rapid exchange stent delivery systems, may be used without departing from the scope of the present invention. The catheter assembly 32 of FIG. 4 is used to implant the self-expanding stent 30 in the body vessel 34 using an over-the-wire or rapid-exchange catheter configuration. In one embodiment, as depicted in FIGS. 4-6, the over-the-wire catheter 30 has a guide wire lumen 36 which extends through the catheter and is configured to receive guide wire 38. In order to implant a self-expanding stent 30, the guide wire 38 is positioned in a patient's body vessel 34 and typically extends past stenosed regions 40 in the vessel. In use, the physician manipulates the proximal end of the guide wire which is located outside the patient (not shown) and catheter 32 is advanced along the guide wire 38 until distal end 42 of catheter 32 is positioned within stenosed regions 40. The body vessel 34 includes a main vessel 44 which branches into two smaller diameter side branches 46 and 48. As can be seen in FIG. 4, the catheter 32 extends through the main vessel 44 and into the side branch 48. Stenosed regions 40 are located both in the side branch 48 and the main vessel 44.

As depicted in FIGS. 5 and 6, the self-expanding stent 30 is implanted in stenosed regions 40 by moving an outer delivery sheath 50 in a proximal direction relative to an inner member 52 onto which the stent 30 is mounted. As the proximal end of the deliver sheath 50 is retracted proximally by the physician, the self-expanding stent 30 becomes uncovered and immediately expands radially outwardly to contact the vessel wall in the area of stenosis (see FIG. 5). When fully deployed and implanted, as shown in FIG. 6, the stent 30 will support and hold open stenosed regions 40 so that blood flow is not restricted. After the stent 30 is implanted, the over-the-wire catheter is withdrawn from the patient's vasculature.

The stent 30 can be manufactured to have its stiffness differentiated such that one end is softer and more malleable than the other end so that the stent can be advantageously deployed providing support and primary stenting across a bifurcated blood vessel 34. As can be seen in FIG. 6, a stent 30 made in accordance with the present invention includes an end implanted in the smaller diameter side branch 48 which is made softer and more malleable than the opposite end which is deployed and implanted in the larger diameter main vessel 44. In this manner, the stiffness, and the corresponding outward radial force applied by stent 30 at the side branch 48 is much less than the radial force developed and applied by the stent at the larger diameter main branch 44. In this manner, there is less possibility that trauma can be inflicted to the lining of the side branch 48 once the stent is implanted in the patient. Prior art stents maintain a uniform stiffness and exert a uniform outward radial force once expanded, could possibly cause more force to be applied at the side branch than is needed. As a result, the chances of trauma being caused by such a stent is increased. A stent having stiffness differentiated in accordance with the present invention is thus able to support the bifurcated vessel without causing the end of the stent in the smaller vessel to become embedded in the vessel tissue.

Referring now to FIG. 7, a medical device, such as a self-expanding stent 60, is shown with the ends 62 and 64 of the stent covered by a device, such as a heat sink or a heat source 66 which can be utilized to supply the necessary heat treatment to the desired areas of the structural element forming the device. Again, the medical device made in accordance with the present invention is shown as a self-expanding stent and the ends of the stent are shown being heat treated. However, it should be appreciated that other portions of the stent could be heat treated to change the transition temperature and achieve the necessary level of stiffness which is desired across the stent. This would be true with any structural element utilized to create a medical device made in accordance with the present invention.

Referring now to FIG. 8, the medical device shown as a stent 60 is mounted onto a rotatable mandrel 68. This mandrel acts like a heat sink and a support mounting which allows the heat treating process to be automated so that the medical device can be more easily manufactured. Again, a heating source 70 such as an applied voltage generator and electrodes 72 are used to heat treat the select portions of the medical device. The electrodes 72 can be made to move in a three-dimensional range allowing the electrodes to be selectively positioned across the area to be heat treated. The rotation of the mandrel 68 also allows the medical device to be positioned in relationship to the electrodes 72 to automate the heat treatment procedure. It should be appreciated that other devices for automating this heat treat process can be developed in accordance with the present invention.

The aforementioned delivery system in FIGS. 4-6 is merely intended to be an example of a delivery system that may be used in combination with the present invention, hence is not limited to solely that type of delivery system. Thus, nearly any type of delivery system may be contemplated for use with the present invention.

The medical device of the present invention can be made in many ways. One particular method of making the device is to cut a thin-walled tubular member, such as nickel-titanium hypotube, to remove portions of the tubing to form the desired pattern of the structural element, leaving relatively untouched the portions of the tubing which form the structural element. The tubing may be cut into the desired pattern by means of a machine-controlled laser. Those skilled in the art also will realize that the medical device can be laser cut from a flat sheet of nickel-titanium alloy. When a stent is to be manufactured, the laser cut sheet can be rolled up in a cylindrical configuration with the longitudinal edges welded to form a cylindrical member. Again, the structural element could be formed from a single piece or a plurality of strands of nickel-titanium alloy.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished medical device. The medical device can be laser cut much like a stent is laser cut. Details on how the tubing can be cut by a laser are found in U.S. Pat. Nos. 5,759,192 (Saunders), 5,780,807 (Saunders) and 6,131,266 (Saunders) which are hereby incorporated by reference in their entirety.

The process of cutting a pattern into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is usually set between about 0° C. and 20° C. in order to achieve superelasticity at human body temperature. The austenite temperature can be measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of nickel-titanium can be utilized, as can other self-expanding alloys, to obtain the desired features.

While several particular forms of the invention have been illustrated and described, it will also be apparent that various modifications can be made without departing from the spirit and scope of the invention. Accordingly, it is not intended that the invention be limited, except as by the appended claims.

What is claimed is:

1. A medical device for delivery to, or deployment within, a body vessel of a mammalian body, comprising:
   a structural element formed from a single piece of superelastic material and having a restrained shape, a deployed shape and an adjustable transition temperature wherein the structural element transitions between a relatively malleable phase and a relatively stiff phase, the structural element including:
   a first portion forming part of the structural element and having a transition temperature adjusted so as to cause the first portion to be in the relatively stiff phase when the structural element is subjected to the body temperature of the mammalian body; and
   a second portion forming part of the structural element and having a transition temperature adjusted so as to cause the second portion to be in the relatively malleable phase when the structural element is subjected to the body temperature of the mammalian body.

2. The medical device of claim 1, wherein the transition temperatures of all portions of the structural element are below body temperature.

3. The medical device of claim 1, wherein the transition temperatures of certain portions of the structural element are below body temperature while other portions of the structural element device have a transition temperature above body temperature.

4. The medical device of claim 1, wherein the transition temperatures of all portions of the structural element are above body temperature.

5. The medical device of claim 1, wherein the structural element has a central portion and a pair of ends, the central portion of the structural element has a lower transition temperature than the end portions of the structural element, whereby the central portion assumes the relatively stiffer state than the ends of the structural element which remain in relatively malleable state when the structural element is subjected to body temperature.

6. The medical device of claim 1, wherein one end portion of the structural element has a higher transition temperature than the opposite end portion of the structural element, whereby the one end portion of the structural element assumes the relatively malleable state than the opposite end portion of the structural element when the structural element is subjected to body temperature.

7. The medical device of claim 6, wherein the transition temperature gradually decreases along the structural element from one end portion to the opposite end portion.

8. The medical device of claim 6, wherein the transition temperature abruptly decreases at a point between the one end portion and the opposite end portion of the structural element.

9. The medical device of claim 1, wherein the structural element comprises a structure of struts wherein selected struts have a higher transition temperature than other struts whereby the stiffness of the structural element is reduced without a commensurate reduction in radial stiffness upon being subjected to body temperature.

10. The medical device of claim 1, wherein the superelastic material is Nitinol which undergoes a transition from its martensitic phase to its austenitic phase as its temperature is increased through a transition zone and wherein A(f) designates the temperature at which such transition is completed.

11. The medical device of claim 10, wherein the A(f) transition temperature of selected portions of the structural element is about 20 C higher than other portions of the structural element, whereby an approximately 50% difference in stiffness is achieved when the structural element is subjected to body temperature.

12. The medical device of claim 11, wherein the A(f) transition temperature of selected portions of the structural element is 0 C to 10 C while other portions of the structural element have an A(f) transition temperature of 20 C to 30 C.

13. The medical device of claim 1, wherein the structural element is formed into a stent.

14. The medical device of claim 1, wherein the A(f) transition temperature of selected portions of the structural element is about 0 C to 25 C.

15. The medical device of claim 1, wherein the A(f) transition temperature of selected portions of the structural element is about 40 C to 60 C.

* * * * *

UNITED STATES PATENT AND TRADEMARK OFFICE
CERTIFICATE OF CORRECTION

PATENT NO. : 7,632,303 B1 Page 1 of 1
APPLICATION NO. : 10/152150
DATED : December 15, 2009
INVENTOR(S) : Stalker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1844 days.

Signed and Sealed this

Second Day of November, 2010

David J. Kappos
*Director of the United States Patent and Trademark Office*